(12) United States Patent
Winkowski

(10) Patent No.: US 8,778,385 B1
(45) Date of Patent: Jul. 15, 2014

(54) MEDICATED ANIMAL FOOD COMPOSITION

(71) Applicant: Lynda Winkowski, Coral Springs, FL (US)

(72) Inventor: Lynda Winkowski, Coral Springs, FL (US)

(73) Assignee: I Care for Dogs Corp., Sunrise, FL (US)

( * ) Notice: Subject to any disclaimer, the term of this patent is extended or adjusted under 35 U.S.C. 154(b) by 0 days.

(21) Appl. No.: 13/923,834

(22) Filed: Jun. 21, 2013

Related U.S. Application Data

(62) Division of application No. 11/130,447, filed on May 16, 2005, now abandoned.

(51) Int. Cl.
| | | |
|---|---|---|
| *A01N 43/04* | (2006.01) | |
| *A61K 31/70* | (2006.01) | |
| *A23K 1/17* | (2006.01) | |
| *A23K 1/165* | (2006.01) | |

(52) U.S. Cl.
CPC ........................................ *A23K 1/17* (2013.01)
USPC ............................................ 424/442; 514/30

(58) Field of Classification Search
CPC ....................................................... A23K 1/17
USPC ............................................ 424/442; 514/30
See application file for complete search history.

(56) References Cited

U.S. PATENT DOCUMENTS

| | | |
|---|---|---|
| 3,681,504 A | 8/1972 | Johnston et al. |
| 4,039,687 A | 8/1977 | Weyn |
| 4,048,268 A | 9/1977 | Ludwig |
| 4,536,494 A | 8/1985 | Carter |
| 5,030,458 A | 7/1991 | Shug et al. |
| 5,468,735 A | 11/1995 | Schadewald et al. |
| 5,894,029 A | 4/1999 | Brown et al. |
| 6,716,448 B2 | 4/2004 | Huber et al. |
| 6,783,777 B2 | 8/2004 | Miller et al. |
| 2004/0247568 A1 | 12/2004 | Guerino et al. |

FOREIGN PATENT DOCUMENTS

| | | |
|---|---|---|
| EP | 1247456 A2 | 10/2002 |
| EP | 1262185 A1 | 12/2002 |

OTHER PUBLICATIONS

Anderson et al., Toxicological studies on tylosin: its safety as a food additive. Food Cosmet Toxicol. Feb. 4, 1966;(1):1-15.
Grahn et al., History and clinical signs. Can Vet J. Apr. 1998;39(4):247-8.
Reussner et al., Effects of dietary moisture on the determination of the nutritional value of foods. J Nutr. Dec. 1964;84:331-4.
Scott et al., Efficacy of tylosin tablets for the treatment of pyoderma due to *Staphylococcus intermedius* infection in dogs.Can Vet J. Oct. 1994;35(10):617-21.

*Primary Examiner* — Benjamin Packard
(74) *Attorney, Agent, or Firm* — Brian J. Colandreo; Pamela K. Soggu; Holland & Knight LLP

(57) ABSTRACT

A medicated animal food composition suitable for eliminating or reducing tear staining in animals is disclosed. The medicated animal food composition includes an edible animal food product base and a pharmaceutically effective quantity of an antibiotic provided in the animal food product base to substantially reduce bacteria in the tears of the animal. The medicated animal food composition is palatable and appetizing to dogs and other animals and can be eaten to eliminate or substantially reduce tear staining associated with excessive tearing.

7 Claims, No Drawings

MEDICATED ANIMAL FOOD COMPOSITION

RELATED APPLICATION

The subject application is Divisional application of U.S. application Ser. No. 11/130,447, filed on May 16, 2005, the contents of which are herein incorporated by reference in its entirety.

FIELD OF THE INVENTION

The present invention relates to animal food compositions. More particularly, the present invention relates to a medicated animal food composition, which is formulated with an antibiotic that prevents or reduces tear staining associated with excessive tearing in dogs or other animals.

BACKGROUND OF THE INVENTION

Excessive tearing, or "epiphora," in canines is manifested by a watery ocular discharge and is a very common concern of pet owners. Environmental, genetic and emotional factors contribute to canine epiphora. In dogs having particularly large eyes or certain facial bone structures, epiphora may be an inherited and irreversible part of their anatomy. Teething puppies exhibit the symptoms of epiphora more frequently than adult dogs. Dogs with small or clogged tear ducts are also particularly prone to epiphora. Fleas are a potential cause of epiphora since they are likely to benefit from the dampness around the dog's eyes. Epiphora in dogs may also be diet-related. Foods with dyes or water having a high mineral content can cause epiphora.

Tear staining associated with epiphora is a common problem. In a recent survey, 89% of Maltese, Bichon, Havanese, Lhasa and Terrier owners indicated that their dogs were afflicted with staining of the facial hair due to excessive tearing. When canine facial hair becomes wet due to excessive tearing, the hair becomes a breeding ground for bacteria and yeast, such as Ptyrosporin or Red Yeast, which causes a deep reddish-brown stain. Such facial hair staining does not indicate a poor quality or a poorly bred, dog, nor is it an indication that the dog is neglected, mistreated or unhealthy. It simply indicates that the dog tears excessively and/or drains tears to a lesser extent than is necessary for any of a number of possible reasons.

An unconstrained ear infection can also be the cause of excessive tearing and facial hair staining. Proper care is necessary to ensure that after bathing, the dog's ears are dried thoroughly. Sporadic growth of hair in the ears should also be gently pulled out using a forceps. Frequent cleaning of a dog's ears can also contribute to prevention of canine ear infections and resultant staining.

Various conventional preventative measures have been undertaken to combat canine tear staining. These include keeping the dog's eyes clean, since tears drain down the dog's face and the exposure of bacteria and fungi to moisture produces skin irritation, infection and odor. In some dog breeds, hair has a tendency to grow from the face and into the eye and cause eye irritation. Moreover, eyelashes can grow at abnormal angles and rub on the eye. Therefore, regular grooming can significantly reduce eye irritation and resultant tearing and staining. Other preventative measures to reduce excessive canine tearing include having the dog checked at least twice a year for ear infections and ear mites, gum infections, common yeast or bacterial infections of the eye (especially Red Yeast) and for clogged tear ducts; maintaining a healthy diet; maintaining good hygiene; and reducing stress.

Although conventional preventative measures are important, they are oftentimes insufficient to eliminate the problem of excessive tearing, since excessive tearing may be due to unchangeable factors such as a dog's heredity or propensity to excessive chewing while cutting new teeth. Medications that treat tear staining are available by prescription. These include Tetracycline, for example. However, a disadvantage associated with the use of Tetracycline to treat excessive tearing is that Tetracycline has a tendency in many canines to cause upset stomach, which contributes to additional tear staining, as well as staining of the teeth.

U.S. Pat. No. 6,716,448 discloses domesticated household pet food that is formulated with ivermectin to provide quantities of ivermectin sufficient to establish and maintain substantially constant concentrations of the drug in a pet's bloodstream.

U.S. Pat. No. 5,894,029 discloses a method of making a pet snack food which includes farinaceous and proteinaceous materials and flavoring ingredients such as seasonings, smoke flavoring, spices and additives such as cyclodextrin, emulsifiers, preservatives, trace minerals, vitamins, and optionally, medications, nutrients and supplements as an inner puffed core matrix encapsulated in an outer shell composed of flavoring ingredients.

U.S. Pat. No. 4,536,494 discloses an animal feed composition that comprises a conventional animal feed and a feed-efficiency-effective amount of natamycin. The feed composition may comprise natamycin in a range of about 0.000055 to 0.011 weight percent. A premix for incorporation into the animal feed preferably comprises about 2-25 grams of natamycin admixed with about one pound of an inert carrier such as rice hulls or calcium carbonate. One pound of the premix is added to about one ton of the conventional animal feed.

U.S. Pat. No. 6,783,777 discloses a method of feeding young, weaned swine including applying a liquid digest onto a feed substance to form a feed material. The liquid digest includes an enzymatically-processed material.

U.S. Patent Publication No. 2004/0247568 discloses methods for the formulation of microbial feed additives with animal feed and methods of administering microbial feed additives.

There is an unmet need for an edible product that is palatable and contributes to the elimination or reduction of tear staining, especially in cases in which conventional measures are ineffective, and which is safe for daily use.

SUMMARY OF THE INVENTION

The present invention is generally directed to a medicated animal food composition which is palatable and appetizing to dogs and other animals and can be eaten to eliminate or substantially reduce tear staining associated with excessive tearing. In one general aspect of the invention, the medicated animal food composition typically comprises:

an edible animal food product base; and a pharmaceutically effective quantity of an antibiotic provided in the animal food product base.

In another aspect of the present invention, the antibiotic is tylosin.

In still another aspect of the present invention, the antibiotic is present in the animal food product base in a quantity of at least about 50% of the antibiotic by weight.

In yet another aspect of the present invention, the antibiotic is present in the animal food product base in a quantity of about 53% of the antibiotic by weight.

In another aspect of the present invention, the medicated animal food composition can be formulated for treatment of dogs, dogs and cats, horses or other animals.

In yet another aspect of the present invention, the medicated animal food product may include any conventional animal food ingredient or a combination of conventional animal food ingredients.

In still another aspect of the present invention, the medicated animal food product may include corn flour, wheat flour, natural chicken liver flavor, lamb meal, chicken, rice flour, powdered cellulose, corn syrup, vegetable oil, mono-glycerides, di-glycerides, food coloring and lecithin.

These and other objects, features, and advantages of the present invention will become more readily apparent from the detailed description of the preferred embodiments, which follow.

DESCRIPTION OF THE PREFERRED EMBODIMENTS

The present invention is directed to a medicated animal food composition which is ingestible and effective in eliminating or at least substantially reducing unsightly tear stains in canines or other animals which is associated with excessive tearing or epiphora. The animal food product is formulated with any conventional animal food ingredient or a combination of conventional animal feed ingredients along with an antibiotic which eliminates or reduces the presence of bacteria in the tears. In a preferred embodiment, the medicated animal food composition has a powdered or ground-up composition and can be sprinkled on or mixed with the animal's food prior to ingestion. About 25 days to about 40 days into the treatment regimen, the dog's tears are essentially stain-free. The medicated animal food composition can be specifically formulated for dogs, dogs and cats, horses or other animals.

The medicated animal food composition may include any edible food product base in combination with an antibiotic such as, but not limited to, tylosin. Suitable edible food product base ingredients include but are not limited to corn flour or wheat flour with natural chicken flavor, lamb meal, chicken or rice flour in combination with an antibiotic, along with powdered cellulose and corn syrup or vegetable oil, mono-glycerides and di-glycerides, various food colors and lecithin. Preferably, the medicated animal food composition includes the ingredients corn flour, wheat flour, natural chicken liver flavor, lamb meal, chicken and rice flour, a pharmaceutically effective concentration of an antibiotic, powdered cellulose, corn syrup, vegetable oil, mono and di-glycerides, brown #9, yellow #5 and lecithin. Most preferably, the medicated animal food composition includes the ingredients corn flour, wheat flour, natural chicken liver flavor, lamb meal, chicken, rice flour, along with the antibiotic tylosin as tartrate, powdered cellulose, corn syrup, vegetable oil, mono and di-glycerides, brown #9, yellow #5 and lecithin. Preferably, the antibiotic is present in the medicated animal food composition in a quantity of at least about 50%, and most preferably, about 53% by weight.

In preparation of the medicated animal food composition, all of the ingredients (except for the tylosin) are initially processed into a powder and then mixed together with the tylosin. Tylosin is available from the Omaha Vaccine Co. under the brand name TYLAN and is a veterinary antibiotic that is FDA-approved for fowl (chickens/turkeys) and swine (pigs). Tylosin is used primarily to treat respiratory disease caused by *Mycoplasma gallisepticum*. It has been found that Tylosin has some beneficial effect in controlling tear staining in Maltese dogs.

In an exemplary packaging arrangement, a single 30-gram (1 oz) quantity of the product is packaged into a single bottle and corresponds to 35 single dosages, although other packaging arrangements are suitable. The relative quantities of the antibiotic and the remaining ingredients of the medicated animal food composition for a 40-gram quantity packaged into a single bottle and a 30-gram quantity of the product packaged into a single bottle are shown in Tables (I) and (I), respectively, below:

TABLE I

| 40 gram quantity | |
| --- | --- |
| Antibiotic | 13.9 g |
| Remaining ingredients | 26.1 g |
| Product | 40 net |

TABLE II

| 30 gram quantity | |
| --- | --- |
| Antibiotic | 10.4 g |
| Remaining ingredients | 19.6 g |
| Product | 30 net |

In typical application, the medicated animal food composition is sprinkled daily (7 days per week) on conventional animal food in a dosage of typically about ½ teaspoon for dogs or cats having a weight of about 3.5 to 7.0 pounds for a period of typically about 3 months. After about 3 months of treatment, dosages may be reduced to 4 times per week. After about 6 months of treatment, dosages may be reduced to about 2 times per week. In the event that tear staining returns, the dosage may be increased to about 3 times per week. The quantity or dosage of the medicated animal food composition which is effective in controlling tear staining in various animals is based on animal size and is listed in Table (III) below:

TABLE III

| | dosages |
| --- | --- |
| Animal | Dosage |
| Puppies & Kittens up to 3 months | ⅛ teaspoon daily |
| Dogs & Cats (up to 3.5 lbs) | ¼ teaspoon daily |
| Dogs & Cats (3.5 to 7.0 lbs) | ½ teaspoon daily |
| Dogs & Cats (7.0 to 10.0 lbs) | ¾ teaspoon daily |
| Dogs & Cats (10+ lbs) | 1 teaspoon daily |

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A method of reducing tear staining comprising:
providing a powdered food product base for one or more of a dog and a cat;
providing a pharmaceutically effective quantity of a tylosin tartrate for preventing staining of hair of the one or more of the dog and the cat caused by contact with tears of the one or more of the dog and the cat;

combining the powdered food product base and the pharmaceutically effective quantity of the tylosin tartrate into a medicated food composition; and administering the medicated food composition to the one or more of the dog and the cat in need thereof.

2. The method of claim 1, wherein the pharmaceutically effective quantity of the tylosin tartrate is provided in a range of between about 15% to about 60% by weight of the powdered food product.

3. The method of claim 1, wherein the pharmaceutically effective quantity of the tylosin tartrate is provided in a range of between about 25% to about 40% by weight of the powdered food product.

4. The method of claim 1, wherein the pharmaceutically effective quantity of the tylosin tartrate is provided in a range of between about 30% to about 35% by weight of the powdered food product.

5. The method of claim 1, wherein the powdered food product base includes one or more of: corn flour, wheat flour, natural chicken flavor, lamb meal, chicken, chicken liver, beef, beef liver and rice flour.

6. The method of claim 1, wherein the powdered food product base includes one or more of: corn syrup, vegetable oil, mono-glycerides, di-glycerides, food coloring and lecithin.

7. The method of claim 1 wherein administering the medicated food composition to the one or more of the dog and the cat includes applying the medicated food composition to one or more of a dog food and a cat food.

\* \* \* \* \*